(12) United States Patent
Landa et al.

(10) Patent No.: US 6,893,630 B2
(45) Date of Patent: May 17, 2005

(54) ANTI-MICROBIAL ANTIPERSPIRANT PRODUCTS

(75) Inventors: Andrew Sjaak Landa, Wirral (GB); Stephen Anthony Makin, Wirral (GB); Victoria Anne McKay, Wirral (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 47 days.

(21) Appl. No.: 09/764,829

(22) Filed: Jan. 17, 2001

(65) Prior Publication Data

US 2001/0046479 A1 Nov. 29, 2001

(30) Foreign Application Priority Data

Jan. 18, 2000 (GB) .............................................. 0001130
Jan. 18, 2000 (GB) .............................................. 0001131

(51) Int. Cl.[7] .............................................. A61K 7/32
(52) U.S. Cl. .......................................................... 424/65
(58) Field of Search ........................................... 424/65

(56) References Cited

U.S. PATENT DOCUMENTS

| | | | | |
|---|---|---|---|---|
| 4,356,190 A | * | 10/1982 | Kraskin ....................... | 424/319 |
| 4,778,671 A | * | 10/1988 | Wusirika .................... | 423/592 |
| 5,516,511 A | * | 5/1996 | Motley et al. ................ | 424/65 |
| 5,705,171 A | | 1/1998 | Iovanni et al. ............... | 424/401 |
| 5,725,846 A | * | 3/1998 | Vu et al. ....................... | 424/65 |
| 5,849,276 A | | 12/1998 | Guskey et al. | |
| 5,939,055 A | | 8/1999 | Vu et al. ....................... | 424/65 |

FOREIGN PATENT DOCUMENTS

| | | |
|---|---|---|
| EP | 0 483 426 | 5/1992 |
| EP | 0736804 | 10/1996 |
| GB | 2091099 | 7/1982 |
| GB | 2097675 | 11/1982 |
| GB | 2109685 | 6/1983 |
| WO | 98/43604 | 10/1998 |
| WO | 99/56717 | 11/1999 |

OTHER PUBLICATIONS

Search Reports under Section 17 Application Nos. GB–0001131.2 and GB 0001130.4 dated May 11, 2000.

* cited by examiner

*Primary Examiner*—Alton Pryor
(74) *Attorney, Agent, or Firm*—Karen E. Klumas

(57) ABSTRACT

Anti-microbial products comprising an antiperspirant active and an amount of transition metal chelator sufficient to enhance the deodorancy performance of said antiperspirant active, are claimed. The transition metal chelator salt improves the anti-microbial performance of the antiperspirant active and the two components can be co-formulated. Particular products are antiperspirant deodorant compositions. Preferred chelator salts have high affinity for iron (III).

15 Claims, No Drawings

ANTI-MICROBIAL ANTIPERSPIRANT PRODUCTS

FIELD OF INVENTION

This invention relates to the field of anti-microbial compositions and to methods of reducing microbial numbers. In particular, this invention is concerned with reducing microbial numbers upon the surface of the human body and thereby reducing body odour. The compositions and methods involved utilise a transition metal chelator together with an antiperspirant active. When used on the human body, the compositions and methods of the invention are of greatest benefit when used on the most malodorous areas of the body, for example the underarm areas or feet.

BACKGROUND

Typically, a deodorising composition will attempt to significantly reduce or prevent body odour by reducing either perspiration or the number of viable micro-organisms on the body surface as represented herein by skin. The former is usually referred to as an antiperspirant composition and the latter a deodorant. Other compositions attempt to mask body malodours using perfumes.

Compositions reducing perspiration often comprise a metal salt, such as an aluminium or zirconium salt, which blocks the sweat pores. This method is very simple and has proven to be beneficial, yet perspiration is rarely reduced by more than 50%.

Deodorants, on the other hand, reduce the numbers of viable micro-organisms on the surface of the skin. It is well known that sweat is usually odourless until it has been degraded by the skin microflora. Typical deodorants include ethanol and triclosan (2',4,4'-trichloro,2-hydroxy-diphenyl ether) which is a well known anti-microbial agent. However, the deodorising effect obtained with such deodorants wears off with the passage of time and the microflora progressively recover their numbers.

There is, therefore, a continuing requirement for effective and long lasting antiperspirant deodorant compositions for the market. The problem to be solved is not simply reducing sweating and initial microbial numbers on the body surface; equally important is maintaining low microbial numbers (particularly low bacterial numbers) on the body surface (particularly in the most malodorous areas, eg. the axilla).

Transition metal chelators have previously been incorporated into antiperspirant deodorant compositions as formulation aids. U.S. Pat. No. 5,516,511 (Procter and Gamble Co.) discloses particular antiperspirant gel compositions in which chelators are used during manufacture to prevent reaction between the active and the primary gellant, the latter component comprising 12-hydroxystearic acid or a derivative thereof. U.S. Pat. No. 5,849,276 (Procter and Gamble Co.) mentions chelators in antiperspirant stick compositions, although such materials are stated to be optional "non-active" components. The gellants exemplified in this patent are again 12-hydroxystearic acid and derivatives thereof, and also N-lauroyl-glutamic acid dibutyl amide and 2-dodecyl-N.N'-dibutyl-succinamide.

Transition metal chelators have also been disclosed in simple deodorant compositions, that is to say, deodorant compositions excluding antiperspirant actives. U.S. Pat. No. 4,356,190 (Personal Products Co.) discloses the use of selected aminopolycarboxylic acid compounds for inhibiting malodour formation; WO 97/01360 (Concat Ltd.) claims a method of inhibiting bacterial growth using particular substituted polyaza compounds that show affinity for first transition series elements; WO 97/44006 (Ciba Speciality Chemicals Holding, Inc.) claims the use of nitrogen-containing complexing agents for the anti-microbial treatment of the skin and of textile fibre materials; and WO 97/02010 discloses the use of chelators selected from the succinic acid, glutaric acid, and phosphonic acid classes as bactericidal compounds.

Other patents indicate that transition metal chelators can improve the efficacy of specific known anti-microbials. WO 98/12399 (Public Health Research Institute of the City of New York) discloses improved performance of lanthionine-containing bacteriocins in compositions also comprising a transition metal chelator. WO 97/09974 (Laboratoire Medix) discloses compositions comprising chlorhexidine and a chelator. EP 0019670 B1 (Glyco Chemicals, Inc.) discloses anti-microbial compositions comprising a condensation product of 5,5-dimethyl hydantoin and formaldehyde in combination with a water-soluble chelating agent selected from ethylenediaminetetraacetic acid (EDTA), diethylenetriaminepentaacetic acid (DTPA) or the alkali metal salts thereof. U.S. Pat. No. 4,199,602 (Economics Laboratory, Inc.) discloses the potentiation of anti-microbial nitroalkanes by aminocarboxylic-type chelating agents. U.S. Pat. No. 5,688,516 (University of Texas System et al) discloses compositions comprising non-glycopeptide anti-microbials (other than vancomycin) in combination with a selection of components, including a chelating agent. WO 99/10017 (University of Texas System et al) discloses a method for controlling the growth of micro-organisms using a chelating agent and an anti-microbial agent. GB 1,420,946 (Beecham Group Ltd.) discloses that the activity of selected phenolic anti-microbials can be vastly increased by certain chelating agents, in particular the disodium salt of EDTA.

SUMMARY OF THE INVENTION

It has been discovered that the combined use of an antiperspirant active and an effective amount of a transition metal chelator gives surprisingly good and long-lasting anti-microbial benefits. When such treatment is applied to the human body, highly effective malodour control results. An important function of the antiperspirant active is to reduce initial microbial numbers on the surface being treated, whilst the transition metal chelator functions to augment the maintenance of low microbial numbers. Surprisingly, it has been found that the two components can be used together without detrimental interactions affecting either the performance of the components or the stability of compositions containing both the components. On application to the human body, additional hygiene and malodour control derive from the antiperspirancy benefit also delivered.

According to a first aspect of the present invention, there is provided an anti-microbial product comprising an antiperspirant active and an amount of transition metal chelator sufficient to enhance the deodorancy performance of said antiperspirant active.

According to a second aspect of the present invention, there is provided a method of controlling microbial numbers comprising the application to a substrate of a product comprising an antiperspirant active and an amount of transition metal chelator sufficient to enhance the deodorancy performance of said antiperspirant active. A particular application of this aspect of the invention is the control of microbial numbers on the surface of the human body, for example skin, and the resulting control of body odour. This particular application also provides a method for reducing perspiration and providing additional control of bacterial numbers on the body surface, eg. skin surface. This method may also be used to deliver enhanced fragrance intensity from a fragrance-containing product according to the invention.

According to a third aspect of the present invention, there is provided a method for the manufacture of an anti-microbial composition comprising the mixing of an antiperspirant active, a transition metal chelator, and a carrier fluid.

DETAILED DESCRIPTION

The antiperspirant active and the transition metal chelator both function as effective anti-microbial agents in this invention. On application to the human body, the reduced perspiration benefit delivered by the antiperspirant active is also beneficial and further contributes to the deodorancy benefit resulting from the anti-microbial performance of the components of the product. Without wishing to be bound by theory, it is hypothesised that after reduction of microbial numbers by the antiperspirant active, the transition metal chelator effectively inhibits the up-take of essential transition metal ion nutrients by the remaining microbes, thereby minimising their re-growth. Surprisingly, there is no detrimental interaction between the antiperspirant active and the transition metal chelator and an excellent anti-microbial and deodorancy performance is obtained from the products of the invention.

It is not essential that the antiperspirant active and the chelator are part of the same composition. The anti-microbial benefit derived from use of the invention may be gained by independent application of the antiperspirant active and the chelator. Such application may be concurrent or consecutive, provided that the treated substrate experiences the presence of both components at the same time. When the components are applied from independent compositions, it is preferred that the product also comprises a means for, and/or instruction for, both of the compositions to be applied to the substrate requiring treatment.

It is preferred that the anti-microbial product of the invention comprises an antiperspirant active and a transition metal chelator that are both present in the same composition. The benefits found with such compositions can include good product aesthetics, lack of product separation, attainment of the desired rheology, visco-stability, good dispensing, and any combination of these benefits or others.

The method of controlling microbial numbers offered by the invention is particularly useful because the benefit can extend for many hours, for example 5 hours, or 24 hours, or even longer, after application of the product to the substrate. When the substrate is the skin of the human body, this can result in an extended deodorancy benefit; that is to say, extended inhibition of generation of human body odour.

The antiperspirant active and the chelator may be present in the composition or compositions of the invention in any form. For example, either or both of the agents may be used neat or may be diluted with a volatile propellant and used as an aerosol; with an additional liquid and used, for example, as a roll-on or squeeze-spray product; or with a thickener or structurant and used, for example, as a cream, gel or solid stick product.

The anti-microbial product of the invention may be applied to the substrate requiring treatment by any means. Frequently, the substrate requiring treatment is a surface. Application of liquid compositions can be by absorption onto a carrier matrix like paper, fabric, or sponge and application by contacting said carrier matrix with the surface. Solid or semi-solid compositions can be applied by direct contact or can be dissolved or dispersed in a liquid medium prior to application. Application can also comprise a combination of any two or more of the above techniques.

Chelators

Preferred transition metal chelators have affinity for iron (III), preferably high affinity for iron (III); that is to say, a binding constant for iron (III) of greater than $10^{10}$, or, for optimum performance, greater than $10^{26}$. The 'iron (III) binding constant' referred to above is the absolute stability constant for the chelator-iron (III) complex. Such values are independent of pH and are measured on the most anionic, fully deprotonated form of the chelator. Measurements can be made potentiometrically, and in a number of other ways. Full details of suitable methods can be found in "Determination and Use of Stability Constants", A. E. Martell and R. J. Motekaitis (VCH, New York, 1989). Tables of applicable values may be found in numerous sources, for example "Critical Stability Constants", R. M. Smith and A. E. Martell (Plenum Pub. Corp., 1977).

Preferred chelators are "micro-molar active"; that is to say, they are able to significantly inhibit the growth of a relevant micro-organism when present, in a medium containing said micro-organism, at a concentration of $3 \times 10^{-6}$ mol.dm$^{-3}$ or less. Inhibition is considered significant when growth of the relevant micro-organism on a supporting medium can be reduced by at least 30%, preferably by at least 45%. When the surface to be treated is human skin, a relevant micro-organism is *Staphlococcus epidermidis* and chelators capable of achieving significant inhibition include diethylenetriaminepentaacetic acid (DTPA) and triethylenetetraaminehexaacetic acid (TTHA), but exclude ethylenediaminetetraacetic acid (EDTA) and trans-1,2-diaminocyclohexane-N,N,N',N'-tetraacetic acid (CDTA).

The chelator may be used in its acid form, but it may also be used as one of its salts.

The iron (III) chelators used in the present invention preferably have acid forms with at least two, more preferably at least four, and most preferably at least five, ionisable acid groups. The acid groups are preferably carboxylic and/or phosphonic, but may be sulphonic or phosphinic, or any mixture of these groups.

Preferred chelators with phosphonic acid groups are, in the acid form, diethylenetriaminepenta(methylphosphonic) acid (DTPMP), ethanehydroxydiphosphonic acid (EHDP), ethylenediaminetetra(methylenephosphonic acid) (EDTMP), and hexamethylenediaminetetra (methylenephosphonic acid) (HMDTMP).

Particularly suitable chelators for use include polycarboxylate compounds, in particular aminopolycarboxylate compounds. The acid forms of the aminopolycarboxylate compounds include EDTA, CDTA, ethylenediaminedisuccinic acid (EDDS). More preferred aminopolycarboxylate chelators have the acid forms DTPA, TTHA, and ethylenebis [2-(2-hydroxyphenyl)glycine] (EDDHA).

The chelators or salts thereof preferably have only moderate molecular weight, by which it is meant that the chelators, in their acid forms, have a molecular weight of less than 1000, more preferably 200 to 800, and most preferably 290 to 580, and in their salt form have a molecular weight of less than 2000, more preferably 300 to 1400, and most preferably 500 to 1000.

The chelator is preferably incorporated into a composition at a level of 0.01% to 10%, more preferably at a level of 0.05% to 5%, and most preferably at a level 0.3% to 3% by weight of the non-volatile components of the composition. Mixtures of chelator salts may also be used. In aerosol compositions comprising greater than 50% by weight of volatile propellant a preferred level of chelator may be 0.5% to 8% by weight of the non-volatile components of the composition.

Herein, non-volatile components are those having a boiling point greater than 20° C. at atmospheric pressure.

As already mentioned, the chelator may be used in its acid form or as one of its salts. Preferred salts, for certain applications, are monovalent alkali metal salts such as sodium and potassium salts. For certain other applications, for example formulation in alcohol-based compositions, salts with organic counter-ions are preferred, for example protonated or quaternised amines. Salts formed using aliphatic amines are generally preferred to those formed from aromatic amines. A further preference is for protonated or quaternised amine cations possessing a $C_1$–$C_{10}$ terminal hydrocarbyl group, wherein a hydrocarbyl group is a radical comprising solely carbon and hydrogen atoms. Such relatively hydrophobic organic counter-ions lead to particularly good compatibility between the chelator salt and the organic anti-microbial.

Preferred protonated or quaternised amine cations of the chelator salts are of formula $R^1R^2R^3R^4N^{(+)}$, wherein $R^1$ is H or $CH_3$; $R^2$, $R^3$, and $R^4$ are each independently H or an aliphatic or aromatic substituent containing 0 to 3 hydroxyl groups, optionally interrupted and/or substituted by functional groups such as ether, amine, ester, or amide; with the provisos that at least one of $R^2$, $R^3$, or $R^4$ comprises a $C_1$–$C_{10}$ terminal hydrocarbyl group, optionally $R^2$ and $R^3$ together forming a ring as the terminal hydrocarbyl group, and that $R^2$, $R^3$, and $R^4$ are not all $CH_2CH(OH)CH_3$ groups.

Particularly preferred chelator-amine salts are salts of 2-amino-2-methyl-1-propanol, cyclohexylamine, diisopropanolamine, or 2-amino-1-butanol.

Partial salts of chelator acids possessing more than one acidic group may also be employed; such salts retain one or more non-ionised acid groups. Also claimed are salts where the cations are in part protonated or quaternised amines and in part some other cation, for example an alkali metal cation, in particular a sodium ion.

Antiperspirant Actives

Antiperspirant actives are preferably incorporated into a composition in an amount of from 0.5–60%, particularly from 5 to 30% or 40% and especially from 5 or 10% to 30 or 35% of the weight of the composition. The ratio of chelator and/or salt thereof to antiperspirant active is preferably from 1:3 to 1:50 and more preferably from 1:5 to 1:25 by weight.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula $Al_2(OH)_xQ_y.wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP 006,739 (Unilever PLC and NV). Some activated salts do not retain their enhanced activity in the presence of water but are useful in substantially anhydrous formulations, i.e. formulations that do not contain a distinct aqueous phase. Aluminium halohydrates as described herein are particularly preferred in aerosol compositions.

Zirconium actives can usually be represented by the empirical general formula: $ZrO(OH)_{2n-nz}B_z.wH_2O$ in which z is a variable in the range of from 0.9 to 2.0 so that the value 2n-nz is zero or positive, n is the valency of B, and B is selected from the group consisting of chloride, other halide, sulphamate, sulphate and mixtures thereof. Possible hydration to a variable extent is represented by wH2O. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have coordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_3CH(NH_2)COOH$.

It is highly desirable to employ complexes of a combination of aluminium halohydrates and zirconium chlorohydrates together with amino acids such as glycine, which are disclosed in U.S. Pat. No. 3,792,068 (Procter and Gamble Co.). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

Other actives that may be utilised include astringent titanium salts, for example those described in GB 2,299,506.

The proportion of solid antiperspirant salt in a composition normally includes the weight of any water of hydration and any complexing agent that may also be present in the solid active. However, when the active salt is in solution, its weight excludes any water present.

If the composition is in the form of an emulsion the antiperspirant active will be dissolved in the disperse phase. In this case, the antiperspirant active will often provide from 3 to 60% by weight of the aqueous disperse phase, particularly from 10% or 20% up to 55% or 60% of that phase.

Alternatively, the composition may take the form of a suspension in which antiperspirant active in particulate form is suspended in the water-immiscible liquid carrier. Such a composition will probably not have any separate aqueous phase present and may conveniently be referred to as "substantially anhydrous" although it should be understood that some water may be present bound to the antiperspirant active or as a small amount of solute within the water-immiscible liquid phase. In such compositions, the particle size of the antiperspirant salts often falls within the range of 0.1 to 200 μm with a mean particle size often from 3 to 20 μm. Both larger and smaller mean particle sizes can also be contemplated such as from 20 to 50 μm or 0.1 to 3 μm.

Additional Components

An additional component that can sometimes augment the efficacy of the composition is a further organic anti-microbial agent. Most of the classes of agents commonly used in the art can be incorporated into compositions of the invention. Levels of incorporation are preferably from 0.01% to 3%, more preferably from 0.03% to 0.5%. Preferred organic anti-microbial agents have a minimum inhibitory concentration (MIC) of 1 mg.ml$^{-1}$ or less, particluarly 200 $\mu$g.ml$^{-1}$ or less, and especially 100 $\mu$g.ml$^{-1}$ or less. The MIC of an anti-microbial agent is the minimum concentration of the agent required to significantly inhibit microbial growth. Inhibition is considered "significant" if an 80% or greater reduction in the growth of an inoculum of a relevant micro-organism is observed, relative to a control medium without an anti-microbial agent, over a period of 16 to 24 hours at 37° C. The "relevant micro-organism" used for testing should be representative of those associated with the substrate to be treated. When the substrate to be treated is human skin, a relevant micro-organism is *Staphylococcus epidermidis*. Other relevant micro-organisms include Coryneform spp., *Salmonella* spp., *Escherichia Coli*, and *Pseudomonas* spp., in particular *P. aeruginosa*. Details of suitable methods for determining MICs can be found in "Antimicrobial Agents and Susceptibility Testing", C.Thornsberry, (in "Manual of Clinical Microbiology", 5$^{th}$ Edition, Ed. A. Balows et al, American Society for Microbiology, Washington D.C., 1991). A particularly suitable method is the Macrobroth Dilution Method as described in Chapter 110 of above publication (pp. 1101–1111) by D. F. Sahm and J. A. Washington II. MICs of anti-microbials suitable for inclusion in the compositions of the invention are triclosan: 0.01–10 $\mu$g.ml$^{-1}$ (J. Regos et al., Dermatologica (1979), 158: 72–79) and farnesol: ca. 25 $\mu$g.ml$^{-1}$ (K. Sawano, T. Sato, and R. Hattori, Proceedings of the 17$^{th}$ IFSCC International Conference, Yokahama (1992) p.210–232). By contrast ethanol and similar alkanols have MICs of greater than 1 mg.ml$^{-1}$. Preferred organic anti-microbials are bactericides, for example quaternary ammonium compounds, like cetyltrimethylammonium salts; chlorhexidine and salts thereof; and diglycerol monocaprate, diglycerol monolaurate, glycerol monolaurate, and similar materials, as described in "Deodorant Ingredients", S. A. Makin and M. R. Lowry, in "Antiperspirants and Deodorants", Ed. K. Laden (1999, Marcel Dekker, N.Y.). More preferred anti-microbials for use in the compositions of the invention are polyhexamethylene biguanide salts (also known as polyaminopropyl biguanide salts), an example being Cosmocil CQ™ available from Zeneca PLC, preferably used at up to 1% and more preferably at 0.03% to 0.3% by weight; 2',4,4'-trichloro,2-hydroxy-diphenyl ether (triclosan), preferably used at up to 1% by weight of the composition and more preferably at 0.05–0.3%; and 3,7,11-trimethyldodeca-2,6,10-trienol (farnesol), preferably used at up to 1% by weight of the composition and more preferably at up to 0.5%.

A carrier fluid is a highly desirable additional component of many of the compositions of the invention. Such materials act as solvents or carriers for the other components of the composition, facilitating their delivery. Water can be used as a carrier fluid, although it is more preferable to use mixtures of water and an alcohol, especially ethanol. Alcohol/water mixtures are particularly suitable carrier fluids in roll-on and pump spray products. Cyclomethicones and other volatile silicones are another class of carrier fluid that may be employed. Examples of this latter class are Dow Corning silicone fluids 344, 345, 244, 245, 246, 556, and the 200 series; Union Carbide Corp. silicones 2707 and 7158; and General Electric silicone SF1202. Alternatively, non-silicone hydrophobic liquids may be employed, such as mineral oils, hydrogenated polyisobutene, polydecene, paraffins, isoparaffins of at least 10 carbon atoms, and aliphatic and aromatic ester iols. Propylene glycol, butylene glycol, and related glycols may also be used. Other alternative carrier fluids include materials having multiple functions, for example isopropyl myristate, isopropyl palmitate, dipropylene glycol, and glycerol. Mixtures of carrier fluids may also be employed to advantage. Compositions preferably comprise carrier fluid at a level of from 30% to 98% by weight, or more preferably from 60% to 97% by weight, of the non-volatile components of the composition.

Structurants and emulsifiers are further additional components of the compositions of the invention that are highly desirable in certain product forms. Structurants, when employed, are preferably present at from 1% to 30% by weight of the composition, whilst emulsifiers are preferably present at from 0.1% to 10% by weight of the composition. In roll-ons, such materials help control the rate at which product is dispensed by the roll ball. In stick compositions, such materials can form gels or solids from solutions or suspensions of the chelator salt in a carrier fluid. Suitable structurants for use in such compositions of the invention include cellulosic thickeners such as hydroxy propyl cellulose and hydroxy ethyl cellulose, and dibenzylidene sorbitol. Emulsion pump sprays, roll-ons, creams, and gel compositions according to the invention can be formed using a range of oils, waxes, and emulsifiers. Suitable emulsifiers include steareth-2, steareth-20, steareth-21, ceteareth-20, glyceryl stearate, cetyl alcohol, cetearyl alcohol, PEG-20 stearate, and dimethicone copolyol. Suspension aerosols, roll-ons, sticks, and creams require structurants to slow sedimentation (in fluid compositions) and to give the desired product consistency to non-fluid compositions. Suitable structurants include sodium stearate, stearyl alcohol, cetyl alcohol, hydrogenated castor oil, synthetic waxes, paraffin waxes, hydroxystearic acid, dibutyl lauroyl glutamide, alkyl silicone waxes, quaternium-18 bentonite, quaternium-18 hectorite, silica, and propylene carbonate. Some of the above materials also function as suspending agents in certain compositions.

Further emulsifiers desirable in certain compositions of the invention are perfume solubilisers and wash-off agents. Examples of the former include PEG-hydrogenated castor oil, available from BASF in the Cremaphor RH and CO ranges, preferably present at up to 1.5% by weight, more preferably 0.3 to 0.7% by weight. Examples of the latter include poly(oxyethylene) ethers.

Certain sensory modifiers are further desirable components in the compositions of the invention. Such materials are preferably used at a level of up to 20% by weight of the composition. Emollients, humectants, volatile oils, non-volatile oils, and particulate solids which impart lubricity are all suitable classes of sensory modifiers. Examples of such materials include cyclomethicone, dimethicone, dimethiconol, isopropyl myristate, isopropyl palmitate, talc, finely-divided silica (eg. Aerosil 200), particulate polyethylene (eg. Acumist B18), polysaccharides, corn starch, C12–C15 alcohol benzoate, PPG-3 myristyl ether, octyl dodecanol, C7–C14 isoparaffins, di-isopropyl adipate, isosorbide laurate, PPG-14 butyl ether, glycerol, hydrogenated polyisobutene, polydecene, titanium dioxide, phenyl trimethicone, dioctyl adipate, and hexamethyl disiloxane.

Fragrance is also a desirable additional component in the compositions of the invention. Suitable materials include conventional perfumes, such as perfume oils and also include so-called deo-perfumes, as described in EP 545,556 and other publications. Levels of incorporation are preferably up to 4% by weight, particularly from 0.1% to 2% by weight, and especially from 0.7% to 1.7% by weight.

It should be noted that certain components of compositions perform more than one function. Such components are particularly preferred additional ingredients, their use often saving both money and formulation space. Examples of such components include ethanol, isopropyl myristate, and the many components that can act as both structurants and sensory modifiers, for example silica.

Further additional components that may also be included are colourants and preservatives at a conventional concentration, for example $C_1$–$C_3$ alkyl parabens.

Product Forms

The compositions of the invention may take any form. Examples include wax-based sticks, soap-based sticks, compressed powder sticks, roll-on suspensions or solutions, emulsions, gels, creams, squeeze sprays, pump sprays, and aerosols. Each product form contains its own selection of additional components, some essential and some optional. The types of components typical for each of the above product forms may be incorporated in the corresponding compositions of the invention.

Particular embodiments of the invention are anti-microbial products comprising an antiperspirant active and an amount of transition metal chelator sufficient to enhance the deodorancy performance of said antiperspirant active, that are not gel-solid stick compositions gelled by 12-hydroxystearic acid, esters of 12-hydroxystearic acid, amides of 12-hydroxystearic acid, N-lauroyl-glutamic acid dibutyl amide, and 2-dodecyl-N,N'-dibutyl-succinamide.

Embodiments of the invention of this type include liquid and soft solid, compositions. The former compositions may be defined by their ability to flow, whilst the latter compositions may be defined by their lack of hardness, having a hardness less than the lesser of 75 grams of force, as measured by the technique described in U.S. Pat. No. 5,516,511 (Procter and Gamble), or 500 grams of force, as measured by the technique described in U.S. Pat. No. 5,849,276 (Procter and Gamble). Hence, particular embodiments of the invention comprise liquid and soft solid compositions having a hardness such that the pressure required to penetrate the composition is less than 0.06 $N.mm^{-2}$.

The various product forms of the invention each have additional components that are desirably present. Roll-on compositions of the invention preferably have a low level of non-volatile emollient present, for example isopropyl myristate or propylene glycol at 0.2–2%. by weight. Antiperspirant sticks have cyclomethicone as the most preferred carrier fluid. Also preferably present are one or more ethers or esters previously mentioned as sensory modifiers; these materials can serve to mask deposits. Wash-off agents are also desirable in such compositions.

Aerosol Compositions

Aerosol compositions of the invention are a particularly preferred product form. Preferably the propellant is the major component in such compositions, comprising from 30 to 99 parts by weight, more preferably from 50 to 95 parts by weight.

The propellant is normally selected from liquified hydrocarbons or halogenated hydrocarbon gases (particularly fluorinated hydrocarbons such as 1,1-difluoroethane and/or 1-trifluoro-2-fluoroethane) that have a boiling point of below 10° C. and especially those with a boiling point below 0° C. It is especially preferred to employ liquified hydrocarbon gases, and especially $C_3$ to $C_6$ hydrocarbons, including propane, isopropane, butane, isobutane, pentane and isopentane and mixtures of two or more thereof. Preferred propellants are isobutane, isobutane/isopropane, isobutane/propane and mixtures of isopropane, isobutane and butane.

Other propellants that can be contemplated include alkyl ethers, such as dimethyl ether or compressed non-reactive gasses such air, nitrogen or carbon dioxide.

The base composition, which is mixed with the propellant, may comprise any of the following components as preferred additional ingredients: a carrier fluid, a fragrance, an emollient (eg. isopropyl myristate or propylene glycol) or an anticlogging agent (in order to prevent or minimise the occurrence of solid occlusions in the spray nozzle). Further components may be added to mask powdery deposits, for example non-volatile oils, long chain alcohols (eg. octyl dodecanol), ethers (eg. PPG-14 butyl ether), or dimethicone fluids.

The aerosol composition is usually filled into an aerosol canister that is capable of withstanding pressures generated by the formulation, employing conventional filling apparatus and conditions. The canister can conveniently be a metal canister commercially available fitted with a dip tube, valve and spray nozzle through which the formulation is dispensed.

Methods of Manufacture

The details of the relevant methods of manufacture depend upon the product form concerned. The basic method comprises the mixing of an antiperspirant active, a transition metal chelator, and usually a carrier fluid. Other components are optionally added, according to the form of composition desired.

EXAMPLES (Note that "letter" codes refer to Comparative Examples.)

Preparation of Aerosol Antiperspirant Deodorants

Example 1 (see Table 1B) was prepared in the following manner. 0.54 g of quaternium-18-hectorite was gradually added to 5.50 g of volatile silicone fluid (DC 245, ex. Dow Corning), whilst shearing at a speed of ca. 8000 rpm on a Silverson L4RT mixer (ex. Silverson, Chesham, Bucks.). After approximately 10 minutes, 0.18 g of propylene carbonate was added dropwise to the mixture. After a further 5 minutes of mixing at 8000 rpm, the mixture was removed from the mixer and 0.89 g of DTPA was slowly stirred in. The resulting liquid was mixed for a further 5 minutes and then sealed into a tin plate can, having valve access, and 77.66 g of liquified propellant (CAP 40, ex Calor) was introduced into the can from a propellant 'transfer can', via the valve, using a polyethylene transfer device. Finally, the can was fitted with a suitable actuator to enable effective spray application of the product.

Example 2 (see Table 1B) was prepared in a similar manner to Example 1, with the addition of poly (hexamethylenebiguanide) stearate (PHMBS, as described in WO98/56252 [Unilever PLC and NV]) (previously passed through a 45 um sieve) at the same time as the DTPA.

Comparative Examples A, B, and C (see Tables 1A and 1B) were prepared in a similar manner to Examples 1 and 2, varying the compositions as indicated.

Deodorancy Tests

The deodorancy performance of the compositions detailed below were assessed using the following protocol:

A panel was employed comprising 50 individuals who had been instructed to use control ethanolic deodorant products during the week prior to the test. At the start of the test, panellists were washed with unfragranced soap and test product (1.8 g total weight) applied to one axilla and control product applied to the other (1.8 g total weight). (Product application was randomised to take into account any left/right bias). Panellists were instructed not to consume spicy food or alcohol, and not to wash under their own axillae, during the duration of the test. A minimum of three expert assessors determined the intensity of axillary odour at 5 hours and 24 hours after application, scoring the intensity on a scale of 1–5. After each 24 hour assessment, the panellists were re-washed, and products re-applied, as above. The procedure was repeated 4 times. At the end of the test the data were analysed using standard statistical techniques. The compositions tested and the mean malodour scores observed are detailed in the following Tables. (It must be noted that data illustrated in different Tables cannot be directly compared, being derived using different panellists in different tests.)

TABLE 1A

Antiperspirant vs. Antiperspirant + PHMBS[1]

| Component | | Example A | Example B |
|---|---|---|---|
| AACH[2] | | 5 | 5 |
| DC245[3] | | 7.3 | 7.257 |
| Bentone 38V[4] | | 0.5 | 0.5 |
| Propylene carbonate[5] | | 0.2 | 0.2 |
| PHMBS[1] | | 0 | 0.043 |
| CAP40[6] | | 87 | 87 |
| Mean | 5 hour | 1.83 | 1.91 |
| malodour | 24 hour | 1.89 | 1.96 |
| intensity[7] | | | |

All components are expressed as weight per cent of the total composition.
[1]Poly(hexamethylenebiguanide) stearate.
[2]Activated aluminium chlorohydrate, type A296, ex. Guilini.
[3]Volatile silicone, ex. Dow Corning.
[4]Structurant, quaternium-18-hectorite, ex. Rheox.
[5]Co-structurant.
[6]Propellant, proprietary mix of butane, isobutane and propane, Ex. Calor.
[7]Differences in values not significant at the 95% level. (Minimum differences required for significance at the 95% and 99% confidence levels were:
after 5 hours: 0.09 for 95% level; 0.12 for 99% level;
after 24 hours: 0.10 for 95% level; 0.13 for 99% level.)

The results in Table 1A indicate that the addition of 0.043% PHMBS anti-microbial to 5% AACH antiperspirant does not lead to an improvement in the deodorancy performance.

TABLE 1B

Effect of Added Chelator

| Component | | Example C | Example 1 | Example 2 |
|---|---|---|---|---|
| AACH | | 5 | 5 | 5 |
| DC245 | | 7.2 | 6.2 | 6.16 |
| Bentone 38V | | 0.6 | 0.6 | 0.6 |
| Propylene carbonate | | 0.2 | 0.2 | 0.2 |
| DTPA[1] | | 0 | 1.0 | 1.0 |
| PHMBS | | 0 | 0 | 0.043 |
| CAP40 | | 87 | 87 | 87 |
| Mean malodour | 5 hour | 1.84 | 1.73 | 1.67[1] |
| intensity[2] | 24 hour | 2.05 | 1.90 | 1.88 |

All components are expressed as weight per cent of the total composition.
[1]Diethylenetriaminepentaacetic acid.
[2]The differnce in mean malodour intensities between examples C and 2 was significant at the 99% level after 5 hours. After 24 hours, the differences between C and 1 and C and 2 were both significant at the 99% level. (Minimum differences required for significance at the 95% and 99% confidence levels were:
after 5 hours: 0.12 for 95% level; 0.16 for 99% level;
after 24 hours: 0.12 for 95% level; 0.15 for 99% level.)

The results in Table 1B indicate that the addition of 1% DTPA chelator to 5% AACH antiperspirant leads to a significant improvement in the deodorancy performance. In the presence of 0.043% additional anti-microbial (PHMBS) the difference is significant after 5 hours, as well as after 24 hours. These latter results are in marked contrast to the effect of added PHMBS in the absence of chelator (Table 1A), where no benefit is observed.

The benefits observed after 24 hours indicate that prolonged maintenance of malodour reduction results from the use of the compositions of the invention; this is a direct result of the prolonged anti-microbial activity of the compositions.

Anti-microbial Performance of Chelators

An axillary isolate of Staphylococcus epidermidis was grown overnight in 100 ml of tryptone soy broth (TSB, Oxoid Ltd). 10 ml of this culture was taken and subjected to centrifugation. The separated cells were re-suspended in 10 ml of phosphate buffered saline and the centrifugation procedure repeated. The washed cells were re-suspended in 10 ml of phosphate buffered saline to give the inoculum. 100 µl of the inoculum was added to 100 ml of semi-synthetic medium (SSM) containing $(NH_4)_2SO_4$ (0.066 g), $MgSO_4 \cdot 7H_2O$ (0.012 g), KCl (0.1 g), $KH_2PO_4$ (0.27 g), $Na_2HPO_4$ (1.43 g), thiamin (0.1 mg), biotin (0.05 mg), Peptone P (0.05 g), and glucose (2.0 mmole) which had been previously sterilised by autoclaving at 121° C. for 20 minutes. The pH of the SSM was adjusted to 6.7 with HCl after sterilisation, prior to addition of the inoculum. This control medium was utilised in all of the in vitro inhibition studies. The chelator-containing test media were prepared in a similar manner, the chelator being introduced at a concentration of $3 \times 10^{-6}$ mol.dm$^{-3}$ before the pH adjustment with HCl.

100 µl of the S. epidermidis inoculum was introduced into the control medium and into test media containing the chelators indicated in Table 2. The cultures were inoculated at 37° C. (with agitation at 200 rpm) for 16 hours, and the optical density of the cultures measured at 600 nm to determine the extent of bacterial growth. By comparison of the optical density of the culture in the presence of chelating agent, to that of the control, the percentage inhibition of growth was established. (Optical density measurements were made on 1 in 4 dilutions of the cultures with 0.9% (w/v) saline, using 1 cm path length cuvettes, on a Pharmacia Biotech Ultrospec 200 Spectrophotometer.)

TABLE 2

Results of Anti-microbial Performance Tests

| Chelator | Inhibition of growth (%) |
|---|---|
| EDTA | 0 |
| CDTA | 12.3 |
| DTPA | 56.5 |
| TTHA | 56.3 |

These results indicate that DTPA and TTHA meet the criterion to be considered preferred "micro-molar active" chelators, whilst CDTA and EDTA fail this criterion.

Preparation of Stick Antiperspirant Deodorants

The stick antiperspirant deodorant compositions indicated in Table 3 were prepared in the following manner. The stearyl alcohol, hydrogenated castor oil, volatile silicone DC245, and PEG-8 distearate were heated under reflux at 85° C., with stirring, until all solids were melted. To the mixture was added Suprafino talc and the antiperspirant salt. For Examples 3 and 4, the DTPA and Cosmocil stearate were added at this point. Stirring was continued and the temperature was allowed to fall to 60° C. On attainment of this temperature, the compositions were transferred to plastic stick barrels and left to solidify.

The deodorancy performance of Example 3 and Comparative Example D were assessed using the aforementioned protocol, with the modification of using only 25 panellists and a product dosage of 0.30 g per axilla.

TABLE 3

Stick Deodorant Antiperspirants

| | | Example | |
|---|---|---|---|
| Component | D | 3 | 4 |
| AZAG[1] | 25.0 | 25.0 | 25.0 |
| Suprafino Talc | 3.2 | 3.2 | 3.2 |
| Stearyl alcohol[2] | 14.0 | 14.0 | 14.0 |
| Hydrogenated Castor Oil[3] | 4.0 | 4.0 | 4.0 |
| PEG-8 distearate[4] | 1.0 | 1.0 | 1.0 |
| DTPA | 0 | 1.0 | 3.0 |
| Cosmocil Stearate[5] | 0 | 0.215 | 0.215 |
| Volatile Silicone DC245[6] | to 100 | to 100 | to 100 |
| Mean malodour intensity[7] 5 hour | 1.60 | 1.41 | — |
| Mean malodour intensity[7] 24 hour | 1.77 | 1.70 | — |

All components are expressed as weight per cent of the total composition.
[1]Antisprant salt: AZAG Q-57167.
[2]Lanette C-18 DEO.
[3]Castorwax MP80.
[4]Estol E040DS.
[5]Polyhexamethylene biguanide.
[6]Cyclomethicone.
[7]The difference after 5 hours was significant at the 95% level. (Minimum differences required for significance at the 95% and 99% confidence levels were:
after 5 hours: 0.16 for 95% level; 0.20 for 99% level;
after 24 hours: 0.14 for 95% level; 0.18 for 99% level.)

What is claimed is:

1. An anti-microbial product comprising a composition comprising an antiperspirant active and an iron (III) chelator, wherein the antiperspirant is selected from the group consisting of an aluminum, zirconium or mixed aluminum/zirconium salt and wherein the iron (III) chelator is selected from the group consisting of diethylenetriaminepentaacetic acid (DTPA) and triethylenetetraaminehexaacetic acid (TTHA).

2. An anti-microbial product according to claim 1, having a hardness such that the pressure required to penetrate the composition is less than 0.06 N.mm$^{-2}$.

3. An anti-microbial product according to claim 1, comprising an aerosol composition.

4. An anti-microbial product according to claim 3, wherein an aluminium halohydrate is a component of the aerosol composition.

5. An anti-microbial product according to claim 1, wherein the antiperspirant active is an aluminium halohydrate.

6. An anti-microbial product according to claim 1, comprising an additional organic anti-microbial agent.

7. An anti-microbial product according to claim 6, comprising a polyhexamethylene biguanide salt, triclosan, or farnesol.

8. An anti-microbial product according to claim 1, comprising fragrance material at up to 4% by weight of the composition.

9. A method of controlling microbial numbers, said method comprising the application to a substrate the product according to claim 1.

10. A cosmetic method of reducing perspiration and providing additional control of bacterial numbers on a human body surface, said method comprising the topical application to the human body the products according claim 1.

11. A cosmetic method according to claim 10, resulting in reduced body odour.

12. A cosmetic method of delivering enhanced fragrance intensity comprising the topical application to the surface of the human body the product according to claim 8.

13. A method for the manufacture of an anti-microbial product according claim 1 comprising the mixing of the antiperspirant active, the Fe(III) chelator, and a carrier fluid.

14. An anti-microbial product according to claim 1, wherein the iron (III) chelator is diethylenetriamineepentaacetic acid or a salt thereof.

15. An anti-microbial product according to claim 1, comprising a wash-off agent.

* * * * *